US010154969B2

(12) United States Patent
Ribeiro Dos Santos et al.

(10) Patent No.: US 10,154,969 B2
(45) Date of Patent: Dec. 18, 2018

(54) TRANSDERMAL DEVICE INCLUDING POROUS MICROPARTICLES (71) Applicant: PIERRE FABRE MEDICAMENT, Boulogne-Billancourt (FR)

(72) Inventors: Isabel Ribeiro Dos Santos, Eaunes (FR); Michel Sournac, Toulouse (FR)

(73) Assignee: PIERRE FABRE MEDICAMENT, Boulonge-Billancourt (FR)

(*) Notice: Subject to any disclaimer, the term of this patent is extended or adjusted under 35 U.S.C. 154(b) by 19 days.

(21) Appl. No.: 14/382,274

(22) PCT Filed: Feb. 28, 2013

(86) PCT No.: PCT/EP2013/054047
§ 371 (c)(1),
(2) Date: Aug. 29, 2014

(87) PCT Pub. No.: WO2013/127929
PCT Pub. Date: Sep. 6, 2013

(65) Prior Publication Data
US 2015/0045748 A1 Feb. 12, 2015

(30) Foreign Application Priority Data
Mar. 2, 2012 (FR) .................... 12 51940

(51) Int. Cl.
*A61K 9/70* (2006.01)
*A61K 31/465* (2006.01)
(Continued)

(52) U.S. Cl.
CPC .......... *A61K 9/7046* (2013.01); *A61K 9/1635* (2013.01); *A61K 9/7038* (2013.01);
(Continued)

(58) Field of Classification Search
CPC .............. A61K 2300/00; A61K 9/7084; A61K 9/7092; A61K 31/00
See application file for complete search history.

(56) References Cited

U.S. PATENT DOCUMENTS 4,548,990 A * 10/1985 Mueller ............... A61K 9/1635
424/486
5,028,435 A * 7/1991 Katz .................... A61K 9/7023
424/447
(Continued)

FOREIGN PATENT DOCUMENTS

EP 0306236 A2 3/1989
EP 0708627 A1 5/1996
(Continued)

OTHER PUBLICATIONS

International Search Report (Forms PCT/ISA/220 and PCT/ISA/210) for International Application No. PCT/EP2013/054047, dated Jun. 10, 2013.
(Continued)

*Primary Examiner* — Johann R Richter
*Assistant Examiner* — Danielle D Sullivan
(74) *Attorney, Agent, or Firm* — Birch, Stewart, Kolasch & Birch, LLP (57) ABSTRACT The present invention relates to a transdermal device including porous microparticles capable of containing an active principle, in particular nicotine, and to the use thereof as a drug, in particular for tobacco cessation. The present invention further relates to a method for preparing a transdermal device including porous microparticles filled with an active principle.

26 Claims, 4 Drawing Sheets

(51) Int. Cl.
*A61K 9/16* (2006.01)
*B32B 37/24* (2006.01)
*B32B 38/00* (2006.01)
*A61K 9/14* (2006.01)

(52) U.S. Cl.
CPC .......... *A61K 9/7053* (2013.01); *A61K 9/7061* (2013.01); *A61K 9/7069* (2013.01); *A61K 31/465* (2013.01); *B32B 37/24* (2013.01); *B32B 38/0004* (2013.01); *B32B 38/164* (2013.01); *A61K 9/146* (2013.01); *A61K 9/7076* (2013.01); *B32B 2037/243* (2013.01); *B32B 2398/00* (2013.01); *B32B 2556/00* (2013.01); *Y10T 156/1052* (2015.01)

(56) References Cited

U.S. PATENT DOCUMENTS

| | | | |
|---|---|---|---|
| 5,145,675 | A | 9/1992 | Won |
| 5,156,843 | A | 10/1992 | Leong et al. |
| 5,725,876 | A | 3/1998 | Mantelle et al. |
| 8,187,628 | B2 * | 5/2012 | Houze ................ A61K 8/0208 424/448 |
| 8,226,974 | B2 * | 7/2012 | Bracht ................ A61K 9/7061 424/443 |
| 2011/0189239 | A1 * | 8/2011 | Mansouri ............ A61K 31/525 424/400 |

FOREIGN PATENT DOCUMENTS

| | | |
|---|---|---|
| JP | 3-5419 A | 1/1991 |
| JP | 10-306023 A | 11/1998 |
| WO | 88/01164 A1 | 2/1988 |
| WO | 95/01766 A1 | 1/1995 |

OTHER PUBLICATIONS

Parthiban et al., "Microsponge Role in Novel Drug Delivery System," International Journal of Pharmaceutical Research and Development, vol. 3, No. 4, Jun. 2011, pp. 117-125, XP-002685345.

Preliminary French Search Report for French Application No. 1251940, dated Oct. 22, 2012.

Quik et al., "Nicotine and Nicotinic Receptors; Relevance to Parkinson's Disease," NeuroToxicology, vol. 23, 2002, pp. 581-594, XP55062376.

Shah et al., "Transdermal Delivery Systems," Topical Drug Bioavailability, Bioequivalence and Penetration, 1993, p. 53, Clery et al.

Shaha et al., "Microsponge drug delivery: A Review," International Journal of Research Pharmacology, vol. 1, Issue 2, 2010, pp. 212-218, XP55041141.

\* cited by examiner

TRANSDERMAL DEVICE INCLUDING POROUS MICROPARTICLES

The present invention relates to the field of porous polymeric microparticles and the use thereof in association with nicotine in a transdermal delivery system. The present invention further relates to a transdermal device containing said porous microparticles and the use thereof as a drug.

Several families of solid polymers (polyamides, polyacrylonitriles, polyacrylic, polyvinylidene chloride, cross-linked copolymers, vinyl chloride, etc.) are known for their cosmetic uses as structuring agents, texturing agents, sebum absorbing agents, and mattifying agents. In each of these cases, it is a matter of formulating a cosmetic product to facilitate application, to give it a particular organoleptic property or to enable local delivery of an active principle.

The technology disclosed in the patent of Advanced Polymer Systems Inc. makes it possible to obtain solid porous particles (or microparticles) by polymerization (for example U.S. Pat. No. 5,145,675 and U.S. Pat. No. 5,156,843).

The polymers according to these patents of Advanced Polymer Systems Inc. are in particular comprised of monomer units such as styrene, divinylbenzene, methyl methacrylate, ethylene glycol dimethacrylate, 4-vinylpyridine, lauryl methacrylate, allyl methacrylate, glycol dimethacrylate. A particular polymer based on cross-linked methyl methacrylate/ethylene glycol dimethacrylate copolymers in microparticle form is marketed under the name Microsponge®.

These porous particles have a unit size varying between 10 and 400 μm and thus may physically entrap large quantities of active principles and then release them in an essentially controlled manner over time. For example, a typical 25 μm Microsponge® sphere may have up to 250,000 pores, resulting in a total pore volume of nearly 1 ml/g. More often, this capacity is characterized by a specific surface measurement expressed in $m^2/g$ of product. Because of their size, these microparticles cannot cross the stratum corneum. These active agents are released by simple diffusion or via several stimuli (mechanical friction, hydration, pH, temperature) which have been disclosed.

This technology is more particularly suited for the formulation of topical drug products (creams, gels, lotions, powders, soaps, etc.) or beauty care products. In both cases, the Microsponge® products improve skin tolerance. For example, in medical dermo-cosmetics, several products are marketed in the form of gels or creams, based on benzoyl peroxide (NeoBenz®), tretinoin (Retin-A® Micro), fluorouracil (Carac® 0.5%) or retinol and hydroquinone (EpiQuin® Micro). For each of these drugs, an additional advantage is to maximize the presence of active principle on the surface of the skin or in the epidermis, while reducing its passing into the dermis.

Compositions calling upon Microsponge® technology have been reported; mention may thus be made of U.S. Pat. No. 5,145,675 and EP 0306236 which disclose how to deliver locally on the skin, and in an extended and controlled manner, certain substances such as sunscreens, repellents, cutaneous steroids such as fluocinonide or benzoyl peroxide, anti-irritants, hair-loss prevention products such as minoxidil or vitamins, essentially. The porous supports used are those disclosed for example in WO 88/01164, that is to say a copolymer of styrene and divinylbenzene or a copolymer of methyl methacrylate and ethylene glycol dimethacrylate or a copolymer of 4-vinylpyridine and ethylene glycol dimethacrylate. These microparticles are obtained in a first step by polymerization in suspension in the presence of a porogenic agent, followed by a step of extraction of this porogen before final incorporation of the active principle.

Microsponge® technology is not used in the formulation of transdermal devices.

The transdermal delivery system, or transdermal device, or patch, uses the cutaneous pathway to provide direct administration of active principle to the blood system without passing by the digestive system, as is the case with tablets or syrups.

A transdermal delivery system is an adhesive device which can administer, for medical purposes, an active substance through the skin.

This system, besides the ease of use it offers, has many advantages.

Firstly, it eliminates the risk of degradation of the drug by gastric juices, hepatic metabolism or the intestinal tract. It is particularly advantageous to provide in patch form molecules that the liver tends to retain. Indeed, if it removes or stores them when they are administered orally, they are diverted from their therapeutic purpose and lose any effectiveness. In parallel, the patch eliminates the risk of digestive disorders related to the ingestion of a substance. Lastly, unlike other devices which result in concentration peaks in the blood system, the patch releases the active substances contained therein with good regularity hour after hour. Consequently, it can maintain a relatively constant concentration of the drug in the body.

It thus maximally reduces the side effects (digestive irritation, for example), the hepatic metabolism (first pass effect) and the intestinal degradation of the drugs in question. Today, a significant number of patches are available for various treatments. In the case of smoking cessation, nicotine is in particular administered using patches.

There are several types of nicotine patches which can be categorized (in *Topical Drug Bioavailability, Bioequivalence and Penetration*, V. P. Shah and H. I. Maibach, published by Springer, 1993, page 53) according to the mechanism by which the active principle is released and to the patch's design. Among the six categories listed, nicotine-based patches are those of categories II, IVa and IVc, alone or in combination. By directly incorporating nicotine in the adhesive, the type IVa patch, as that of the present invention, has the advantage of having a small thickness and of being capable of being cut to size in this exceptional case by virtue of the homogeneous distribution of the active principle across its entire surface, unlike, for example, type II patches comprising a depot region.

Transcutaneous absorption of a substance meets very precise rules taking advantage of patches to control dosing throughout the duration of use. The phenomenon corresponds to the migration of the substance considered from the skin surface to the first capillary layer. But molecules capable of penetrating epidermis are rare. At present, only a dozen administrable by patch are known.

Indeed, their physicochemical characteristics must be such that the skin does not constitute an impassable obstacle; among other things, their molecular mass must be less than 500 daltons, and their melting point must be below 100° C. Furthermore, the candidate substances within the patch must of course be tolerated by the skin, in order to avoid any allergic reaction.

Nicotine's physicochemical properties are problematic for transcutaneous administration; indeed, nicotine base is an oily substance which very quickly penetrates the skin surface to the first capillary layer. Moreover, it is a highly toxic substance. Thus, when the patch is affixed, all of the nicotine contained therein must not pass into the body in just a few minutes: its concentration in the blood must remain constant, at a therapeutic dose, for 12 or so hours. For that, nicotine is formulated in a patch whose composition regulates transfer of the nicotine. Moreover, Fick's law of diffusion may be used to determine a nicotine administration rate, expressed in micrograms per hour and per square centimeter of patch, according to the composition of the patch with which it is associated. The dose injected and the consistency of its administration hour after hour may thus be controlled very precisely. Generally, after a latency period corresponding to the time required for the active principle to cross the epidermis and to reach circulating blood, its concentration rapidly increases exponentially until a state of equilibrium corresponding to the value determined by the patch is reached. This concentration is maintained until the patch is removed or the reserve of active substance is exhausted.

Furthermore, with a patch, treatment may be stopped very easily if the patient exhibits intolerance. It suffices to remove it to end delivery of the drug or of the palliative substance, in the case of nicotine. The principal advantage of the patch remains its ease of use and the regulated delivery over time of the active principle.

In view of the difficulties controlling the release kinetics of nicotine, several devices containing control membranes or solid microparticles have been disclosed. Mention may be made, for example, in EP 708627, of a nicotinic patch including a support layer, a matrix layer comprised of a mixture of nicotine and polymer, said patch being characterized by an average nicotine delivery rate greater than 50 µg/cm$^2$/h. The compositions of patent EP 708627 are characterized by the use of adhesive of the silicone type and solid particles of the silica type.

Other nicotine patch compositions are also known, such as U.S. Pat. No. 5,725,876 disclosing an acrylic-type matrix nicotine patch comprised of clays so as to improve the cohesion of the device. For these two examples, the solid microparticles disclosed are not porous polymers such as those of the present invention.

The applicant sought to design a self-adhesive transdermal device as a substitute for the existing devices. The applicant sought to design a transdermal device capable of controlling the release of nicotine while preserving the attributes of a matrix patch of the "drug in adhesive" type such as small thickness and reduced size, as well as a manufacturing method that is simpler and less expensive than those already known in the prior art.

The applicant sought to solve a certain number of technical problems which existing self-adhesive transdermal devices did not answer:
- obtain a patch characterized by a homogeneous distribution of nicotine in the adhesive matrix, which in an exceptional case allows the patch to be cut to size;
- control plasticization induced by the presence of nicotine, which amounts to maintaining the cohesion of the adhesive matrix;
- improve comfort thanks to a thinner, more flexible patch that is thus more comfortable to use.

Moreover, a certain number of constraints are preferentially to be respected concerning the transdermal device to be obtained:
- control the release of nicotine (to the minimum, avoid a release that is too fast, synonymous with side effects, notably addiction, likely cardiac and of the cutaneous type) with a novel matrix support;
- have good qualities in terms of adhesion and skin tolerance;
- obtain a patch whose aging is of no consequence to the initial physicochemical characteristics of the product;
- select nicotine-compatible components;
- obtain a transparent patch (making it possible to observe possible irritation or local sensitization phenomena).

In a surprising and unexpected manner, the applicant has shown that the use of porous microparticles of solid polymers filled with nicotine in a transdermal delivery system has many advantages, particularly in terms of the controlled release of nicotine and the homogeneous distribution of active principle in the adhesive matrix. Moreover, the use of these microparticles, in a completely unexpected manner, increases cohesion of the patch (notably reducing the risk of leaking and the quantity of matrix residues remaining on the skin after the patch is removed) and reduces the adhesive aggressiveness of the patch.

The present invention also has as an object a method for preparing a transdermal device according to the invention.

The use of microporous solid polymers, in particular those comprised of monomer units such as styrene, divinylbenzene, methyl methacrylate, ethylene glycol dimethacrylate, 4-vinylpyridine, lauryl methacrylate, allyl methacrylate and/or glycol dimethacrylate, have shown very good dispersion within the adhesive and better compatibility with nicotine (no degradation of the active principle, no coloring observed).

Moreover, the method for manufacturing the composition according to the present invention is simpler than that of the manufacture of certain existing self-adhesive transdermal devices such as the Nicotinell® patch, notably described in *Topical Drug Bioavailability, Bioequivalence and Penetration* (V. P. Shah and H. I. Maibach, published by Springer, 1993, page 53), since unlike the latter, the nicotine patch according to the present invention is a monolayer patch which requires only one pass through a coating/drying system.

Furthermore, the object of the present invention differs from certain transdermal nicotine-release devices existing up to now. Indeed, the latter cannot be cut, and moreover, over time, the distribution of nicotine in the patch becomes heterogeneous. Due to maturation, on some patches of the prior art a decreasing and concentric distribution of nicotine from the center toward the periphery may be demonstrated.

A transdermal patch according to the invention contains a homogeneous distribution of nicotine throughout its matrix part. This characteristic allows better use of the device by patients, in particular because the patch is thinner, but also because the patch may be cut to size in order to decrease the dose absorbed without altering its functions.

The characteristics and advantages of the compositions according to the present invention appear in the light of the following description.

The present invention thus relates to a self-adhesive transdermal device, characterized in that it includes the association of a support layer and a self-adhesive matrix layer, and a detachable protective film, said self-adhesive matrix layer including, in relation to the total weight of the self-adhesive matrix layer:

a. 65 to 93% by weight of at least one self-adhesive polymer selected from the group comprising polymers of the acrylic or acrylate type, polymers of the silicone type, polymers of the vinyl acetate type, natural or synthetic gums, copolymers thereof and mixtures thereof;

b. 2 to 15% by weight of at least one microporous solid polymer capable of containing an active principle, said polymer being comprised of monomer units selected from the group of monomers comprising styrene, divinylbenzene, methyl methacrylate, ethylene glycol dimethacrylate, 4-vinylpyridine, lauryl methacrylate, allyl methacrylate, glycol dimethacrylate and mixtures thereof; and c. 5 to 20% by weight of active principle.

By "association" is meant that the layers of the device according to the invention are directly in contact with each other and that once assembled they form a whole which cannot come apart easily and in particular which cannot come apart without human will and intervention.

Preferentially, the patch according to the invention will be of the adhesive monolayer type.

By "support layer according to the invention" is meant any support layer typically used in the field of patches. Preferentially, the support layer is a multilayer film at least one layer of which is a polyester layer and at least one other layer is a polyethylene-based or vinyl acetate ethylene-based layer. Preferentially, the support layer is transparent.

By "detachable protective film" is meant all detachable protective films capable of protecting the device's matrix before the device is used. These films typically used in the field of transdermal devices are well-known to the person skilled in the art. Preferentially, this film is made of siliconized polyester.

The matrix layer according to the invention is self-adhesive. By "self-adhesive" is meant that the matrix layer is able to keep the device according to the invention bound to a support, for example the skin, in a stable manner, with no need for the use of other means of bonding. Preferentially, by "self-adhesive" is meant that the matrix layer allows the device to adhere to the skin for at least 12 hours, preferentially for about 12 to 48 hours, more preferentially for about 24 hours.

The matrix layer according to the invention includes from 65 to 93%, preferentially between 75 and 85% by weight of at least one self-adhesive polymer selected from the group comprising polymers of the acrylic or acrylate type, polymers of the silicone type, polymers of the vinyl acetate type, natural or synthetic gums, copolymers thereof and mixtures thereof.

By "synthetic gum" is meant in particular in the context of the present invention gums selected from the family of elastomers, for example styrene, styrene-isoprene-styrene (SIS), polystyrene-butadiene-styrene (SBS) or styrene-ethylene/butylene-styrene (SEBS). By "natural gum" is meant all types of natural gums such as carrageenan gum or guar gum, for example.

Preferentially, the matrix layer includes at least one polymer of the acrylic or acrylate type.

The polymer of the acrylic or acrylate type according to the invention will preferentially be comprised of monomers selected from the group comprising or consisting of vinyl acetate, 2-ethylhexyl acrylate, butyl acrylate, acrylic acid, methyl methacrylate, methyl acrylate, tert-octyl acrylamide, 2-hydroxy ethyl acrylate, glycidyl methacrylate, or mixtures thereof, more preferentially from the group comprising or consisting of acrylic acid, butyl acrylate, 2-ethylhexyl acrylate, vinyl acetate, and mixtures thereof.

In an embodiment, the self-adhesive polymer according to the invention is an acrylate-vinyl acetate copolymer.

The matrix layer according to the invention further includes from 2 to 15%, preferentially from 5 to 12% by weight in relation to the total weight of the self-adhesive matrix layer of at least one microporous solid polymer capable of containing an active principle.

By "capable of containing an active principle" according to the invention is meant that the microporous solid polymer may be loaded with active principle by adsorption, the active principle is thus associated with the polymer. Preferentially, the microporous solid polymer according to the invention may be loaded with 15% to more than 400%, preferentially more than 50%, for example between 50 and 150%, even for example around 100% or around 140% by weight of active principle in relation to the weight of free microporous solid polymer. The microporous solid polymers according to the invention are preferentially loaded by simple contact (adsorption) with the active principle via mixing.

The microporous solid polymer capable of containing an active principle according to the invention will be preferentially solid porous microparticles of the polymer type or the cross-linked copolymer type (microporous solid polymer).

Preferentially, said microporous solid polymer is comprised of monomer units selected from the group of monomers comprising or consisting of styrene, divinylbenzene, methyl methacrylate, ethylene glycol dimethacrylate, 4-vinylpyridine, lauryl methacrylate, allyl methacrylate, glycol dimethacrylate and mixtures thereof.

Preferentially, the microporous solid polymer is comprised of monomer units of methyl methacrylate and ethylene glycol dimethacrylate. One such polymer may in particular be obtained commercially under the Microsponge® brand. Alternatively, the microporous solid polymer is comprised of monomer units of lauryl methacrylate and glycol dimethyl methacrylate. One such polymer may in particular be obtained commercially under the Polytrap® brand. Preferentially, the self-adhesive transdermal device according to the invention does not contain a microporous solid polymer other than the microporous solid polymer comprised of monomer units of methyl methacrylate and ethylene glycol dimethacrylate or the microporous solid polymer comprised of monomer units of lauryl methacrylate and glycol dimethyl methacrylate.

Preferentially, the microporous solid polymer according to the invention is provided in the form of microparticles of average size comprised between 1 μm and 100 μm, preferentially between 5 μm and 50 μm, more preferentially between 15 μm and 30 μm. The average size may in particular be measured by an apparatus of the laser particle-size analyzer type, for example the Malvern Mastersizer 2000 which, in particular, measures particles ranging from 0.2 μm to 2000 μm in a dry system.

In an embodiment of the invention, the microporous solid polymer according to the invention has a total pore volume comprised between 0.5 and 3 ml/g, preferentially between 1 and 2 ml/g.

In another embodiment, said microporous polymer has a granular pore volume comprised between 0.2 and 3 ml/g, preferentially between 0.5 and 1.5 ml/g, more preferentially between 0.7 and 1.0 ml/g.

Total pore volume and granular pore volume may in particular be measured by a mercury porosimeter, for example the Autopore IV (Micromeritics). These porosimeters make it possible in particular to carry out an intrusion of mercury at constant pressure and thus to be able to determine the total pore volume and granular pore volume of microporous solid polymers. At low pressure (3.45 kPa to 186 kPa, for example), the intrusion volumes obtained correspond to packed powder and total porosity (intergranular and granular). At high pressure (186 kPa to 20.7 MPa, for example), the mercury intrusion values observed correspond to granular porosity.

According to an advantageous characteristic of the present invention, the microporous solid polymer, which is advantageously provided in the form of microparticles, is distributed homogeneously within the self-adhesive polymer mass. According to another characteristic of the invention, the active principle is adsorbed homogeneously in the microporous solid polymer mass. The result is thus regular distribution within the self-adhesive matrix layer of the device of the invention and, therefore, regular release of the active principle.

Preferentially, the device according to the invention is characterized in that the basis weight of the self-adhesive matrix layer is comprised between 50 and 300 g/m$^2$, preferentially between 100 and 200 g/m$^2$.

By "active principle" according to the invention is meant any active principle or any mixture of active principles that may be administered by a device according to the invention. In an embodiment the active principle may be in liquid form, preferentially in the form of an oily liquid. For example, the active principle according to the invention may be selected from the group comprising or consisting of nicotine, nicotinic agonists in particular such as varenicline or cytisine, nitroglycerin, tolbuterol, propanolol, bupranolol, hormones in particular such as estrogens including testosterone, fentanyl, selegiline or lidocaine. In an embodiment the active principle is selected from the group comprising or consisting of nicotine, selegiline, nitroglycerin, tolbuterol, propanolol and bupranolol. The active principle according to the invention is advantageously an active principle the release of which must be slowed or controlled such as, for example, nicotine or selegiline. Preferentially, the active principle according to the invention is nicotine, more preferentially the device according to the invention does not include an active principle other than nicotine.

The active principle may be loaded into the microporous solid polymer in liquid form. The active principle, in particular nicotine, will be preferentially loaded in base form or in the form of a solution of a salt thereof, more preferentially in base form. The quantity of active principle loaded in the particles will depend in particular on the desired quantity of active principle released by the transdermal device according to the invention and on the desired release time. For example, the device according to the invention including nicotine may include between 10 and 100 mg of nicotine, preferentially between 15 and 90 mg of nicotine, for example 15, 30, 45 or 90 mg of nicotine.

The inventors noted that the release of nicotine was particularly well controlled when the microporous solid polymer is as defined in the present invention, preferentially, a methyl methacrylate and ethylene glycol dimethacrylate copolymer, and that the adhesive matrix has a basis weight between 50 and 300 g/m$^2$, preferentially between 100 and 200 g/m$^2$.

The rate of nicotine released by the microporous solid polymers will depend in particular on the nature of the polymer and on pore size. Preferentially, the devices according to the invention allow the release of nicotine from the matrix layer by an average delivery rate comprised between 5 and 100 μg/cm$^2$/h, in an embodiment between 10 μg/cm$^2$/h and 50 μg/cm$^2$/h, for a time interval comprised between 1 and 24 hours. The release rate may be measured by any permeation technique known to the person skilled in the art, in particular via permeation kinetics, for example on abdominal skin of nude mouse arranged on the surface of a glass (Franz) cell, such as in particular described in Example 3.

The matrix layer according to the invention may further include other excipients or components such as antioxidants, for example. In an embodiment, the self-adhesive matrix layer includes at least one antioxidant agent in particular selected from the group comprising or consisting of butyl hydroxy toluene (BHT), butyl hydroxy anisole (BHA), ascorbyl palmitate, alpha tocopherol and esters thereof, citric acid, propyl gallate and mixtures thereof, preferentially BHT. The antioxidant agent is then preferentially present in said self-adhesive matrix layer in a proportion comprised between 0.01 and 1% by weight in relation to the total weight of said self-adhesive matrix layer.

In another embodiment, the self-adhesive transdermal device according to the invention is characterized in that it consists of the association of a support layer and a self-adhesive matrix layer, and a detachable protective film, said self-adhesive matrix layer consisting of, in relation to the total weight of the self-adhesive matrix layer:

a. 65 to 93% by weight of at least one self-adhesive polymer selected from the group comprising polymers of the acrylic type, polymers of the silicone type, polymers of the vinyl acetate type, natural or synthetic gums, copolymers thereof and mixtures thereof;

b. 2 to 15% by weight of at least one microporous solid polymer capable of containing an active principle, said polymer being comprised of monomer units selected from the group of monomers comprising styrene, divinylbenzene, methyl methacrylate, ethylene glycol dimethacrylate, 4-vinylpyridine, lauryl methacrylate, allyl methacrylate, glycol dimethacrylate and mixtures thereof;

c. 5 to 20% by weight of nicotine as active principle;

d. optionally from 0.1 to 1% of an antioxidant agent; and

Preferably, the patch according to the invention will be transparent.

By "transparent" is meant that it makes it possible to sufficiently observe the skin through the patch in order to rapidly identify any possible skin intolerance.

The present invention further relates to a method for preparing a transdermal device according to the invention, characterized in that it comprises or consists of the following steps:

a. Mixing the self-adhesive polymer, the microporous solid polymer, the active principle, preferentially nicotine, and optionally the oxidizing agent, until a homogeneous mixture is obtained;

b. Coating the homogeneous mixture obtained in step a. on a detachable protective film;

c. Gradually drying the coated mixture;

d. Laminating the product obtained in step c. onto a support layer; and e. Optionally, cutting the product obtained in step d. in such a way as to obtain transdermal devices or patches of the desired size.

By mixing the self-adhesive polymer and the microporous solid polymer according to the invention "until a homogeneous mixture is obtained according to the present invention" is meant that the microporous solid polymer must be distributed uniformly in the self-adhesive polymer. This distribution may in particular be evaluated by visual observation (absence of aggregates).

Nicotine may or may not be mixed with the microporous support according to the invention before step a. In a preferred embodiment, nicotine is not mixed with the microporous support prior to step a., the nicotine, the microporous support and the self-adhesive polymer thus being brought into contact independently and concomitantly in step a.

Preferentially, the coating step b. is carried out at a temperature comprised between 30° C. and 50° C.

By "gradually drying" is meant the creation of a temperature gradient. It is preferable that drying occurs gradually in order to avoid crusting. For example, the temperature gradient may be a gradient of 5 to 20° C. in a temperature range from 30° C. to 80° C., preferentially from 40 to 60° C.

After coating and drying, the product obtained in step c. is laminated onto a support layer according to the invention. The lamination operation may be carried out by all methods well-known to the person skilled in the art.

The coated support layer obtained in step d. of the method according to the invention may then optionally be cut to the desired size. For example, the support layer may be cut into transdermal devices or patches (or units) of between 5 $cm^2$ and 80 $cm^2$, for example 10 $cm^2$, 20 $cm^2$, 30 $cm^2$ or 60 $cm^2$.

The transdermal device according to the invention may be packaged in a packaging under a protective (inert) atmosphere, preferentially under nitrogen, in particular when the patch according to the invention does not contain an antioxidant agent. The preparation of inert packaging for patches is well-known to the person skilled in the art and may be carried out by all known methods.

The present invention further relates to a self-adhesive transdermal device according to the invention for use as a drug.

In particular, the present invention relates to a self-adhesive transdermal device according to the invention, preferentially a transdermal device according to the invention containing nicotine, for use in the treatment of nicotine addiction, in particular in order to facilitate smoking cessation.

In another embodiment, the present invention relates to a self-adhesive transdermal device, preferentially a transdermal device according to the invention containing nicotine, for use in the treatment of neurodegenerative diseases such as in particular Parkinson's disease or Alzheimer's disease.

The present invention is illustrated by the examples below which do not limit its scope.

EXAMPLES

Example 1: Characterization of Adsorption Supports

Example 1A: Adsorption Capacity Tests (Table 1)

Comparative tests for measuring the adsorption capacity of nicotine by various microporous solids were carried out. The tests consisted in determining the maximum quantity of nicotine that could be adsorbed on the microporous supports according to the following procedure:

weighing the microporous support, between 0.3 and 2.0 g depending on its density, to have an identical volume, adding nicotine in an iterative manner by weighing out about 0.1 g, impregnating the support with nicotine using a spatula after each addition of nicotine; the appearance of the mixture is then noted.

The maximum adsorption capacity is thus determined: it is the quantity of nicotine adsorbed by the microporous support expressed in grams of nicotine per gram of support, with nicotine seepage not observed.

TABLE 1

| Support type | Trade name | Adsorption capacity (quantity of nicotine in grams/1 gram of support) | Comments - Visual appearance |
| --- | --- | --- | --- |
| Cross-linked MMA/GDMA polymer | Microsponge ® | 1.40 | Significant swelling of particles; light yellow color maintained |
| Silica | Silica shells | 2.70 | Very small particles forming clusters once impregnated |
| Silica | MSS-500/3H4 ® | 3.00 | Difficult homogenization with formation of lumps |
| Densified fumed silica | Aerosil ®V200 | 2.75 | Nicotine penetrates but is not spread out; particles form irregular heaps |
| Polyurethane/silica | BPD 800 ® microspheres | 1.05 | Significant swelling of particles; light yellow color maintained |
| Crospovidone | Polyplasdone ® XL-10 | 0.15 | Nicotine penetrates but is not spread out; significant yellowing |
| Silicone resin/POE lauryl ether 98/2 | DC 9506 ® | 0.60 | Powders that wet well, but tendency to ooze |

The following results were obtained:

As may be noted, the majority of the supports tested combined with nicotine have a large number of disadvantages that make them unusable: spreading is impossible; seepage; formation of aggregates, clusters or lumps.

The cross-linked MMA/GDMA polymers (cross-linked polymer of methyl methacrylate and ethylene glycol dimethacrylate) allow good adsorption of nicotine and have after adsorption a suitable appearance.

Example 1B: Adsorption Support Release Capacity Test (Table 2)

The adsorption supports are loaded with nicotine at 50% or 80% of their maximum adsorption capacity determined beforehand (see preceding Table 1). A wash test is then carried out in order to determine their release capacity expressed in % of nicotine released in relation to the quantity of nicotine added.

The following results were obtained:

TABLE 2

| Support type | Load (%) | Part in the wash (%) |
|---|---|---|
| Silica (Silica shells) | 80% | 90 |
|  | 50% | 96 |
| Cross-linked MMA/GDMA polymer (Microsponge ®) | 80% | 79 |
|  | 50% | 69 |
| Polyurethane/silica (BPD800 ® microspheres) | 80% | 91 |
|  | 50% | 84 |
| Crospovidone (Polyplasdone ® XL-10) | 80% | 99 |
|  | 50% | 89 |
| Silicone resin/POE lauryl ether 98/2 (DC9506 ®) | 80% | 72 |
|  | 50% | 69 |

The wash test is carried out on 200 mg of loaded microparticles, with rinsing carried out with 1 ml of water for a period of 10 seconds with shaking, followed by filtration.

These results show that the cross-linked MMA/GDMA polymers and DC9506® silicone resin retain more nicotine via better adsorption than the other supports.

Example 1C: Adsorption Support Dispersion Tests

Tests of dispersion of the microporous supports are carried out in solvents constituting the majority phase of the adhesive mixtures before coating. These dispersion tests make it possible to verify the technical feasibility of the adhesive mixtures.

These tests are carried out according to the following procedure:

In a 9 ml glass vial, weigh the microporous support, between 0.2 and 1.25 g depending on its density,
add solvent (ethyl acetate or heptane) so as to have a mass ratio of solvent to microporous support equal to about 3,
mix with a spatula and immediately observe the mixture; the mixture is also observed after resting for 48 hours.

The results are presented in Table 3:

TABLE 3

| Support type | Observations with ethyl acetate | Observations with heptane |
|---|---|---|
| Polyurethane/silica (BPD800 ® microspheres) | Liquid suspension | Liquid suspension |
| Crospovidone (Polyplasdone ® XL-10) | Liquid suspension | Liquid suspension |
| Cross-linked MMA/ GDMA polymer (Microsponge ®) | Pasty suspension | Liquid suspension |
| Silica (Silica shells) | Support remains dry | Support remains dry |
| Densified fumed silica (Aerosil ® 200VV) | Support changes appearance: presence of translucent agglomerates | Support remains dry |
| Silica (MSS-500/3H4 ®) | Support changes appearance: presence of translucent agglomerates | Support changes appearance: formation of a gel |
| Silicone resin/POE lauryl ether 98/2 (DC9506 ®) | Support changes appearance: formation of a kind of translucent gel | Support changes appearance: formation of a kind of gum |

The supports of greatest interest at the conclusion of these dispersion tests in solvent are the supports that remain in suspension in either liquid or pasty form: cross-linked MMA/GDMA polymers)) (Microsponge®, BPD800 or Polyplasdone XL10.

Surprisingly, only the cross-linked MMA/GDMA microporous support provides advantageous characteristics in all 3 characterization tests performed. Cross-linked MMA/GDMA microporous polymers are thus, unexpectedly, a support particularly well suited for nicotine (load, release, compatibility).

Example 2: Method for Preparing a Monolayer Transdermal Composition Containing Nicotine and a Microsponge®-Type Microporous Polymer The preparations according to the invention are prepared in the following way:

The adhesive, then nicotine, microporous polymer and optionally BHT are added into a mixing vessel. The stirring parameters (time and speed) are set so as to avoid the formation of lumps and to obtain a homogeneous mixture, and depend in particular on the size of the vessel. After resting for 24 hours, the adhesive mass is coated onto a silicone film in a proportion of 150±5 g/m$^2$ before proceeding to drying at 45° C., which is intended to evaporate the adhesive's solvents, followed by transfer of the matrix onto a transparent polyester support. The product thus obtained is cut into the desired sizes.

Figure 1:
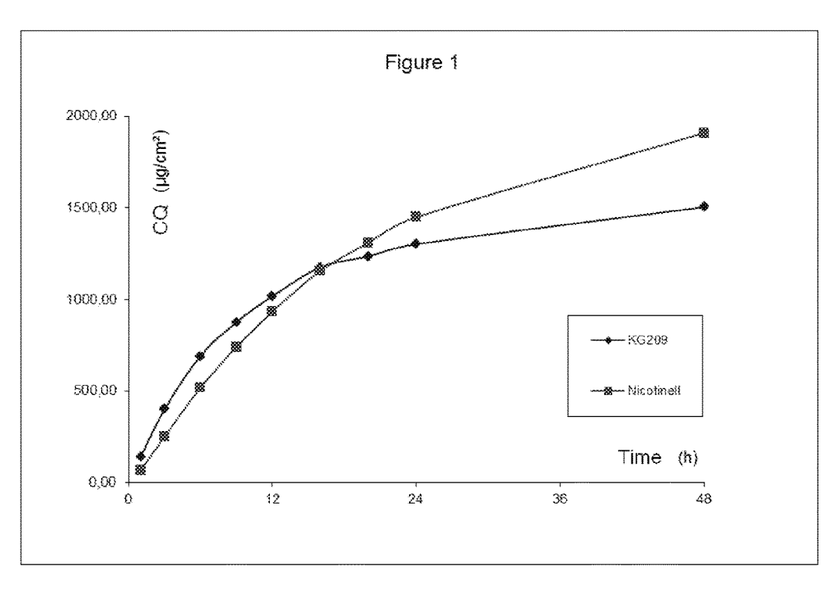
FIGS. 1 and 2: In vitro permeation kinetics showing the effect of the presence of microporous solid polymer (Microsponge®) in the composition according to the invention.
Figure 2:
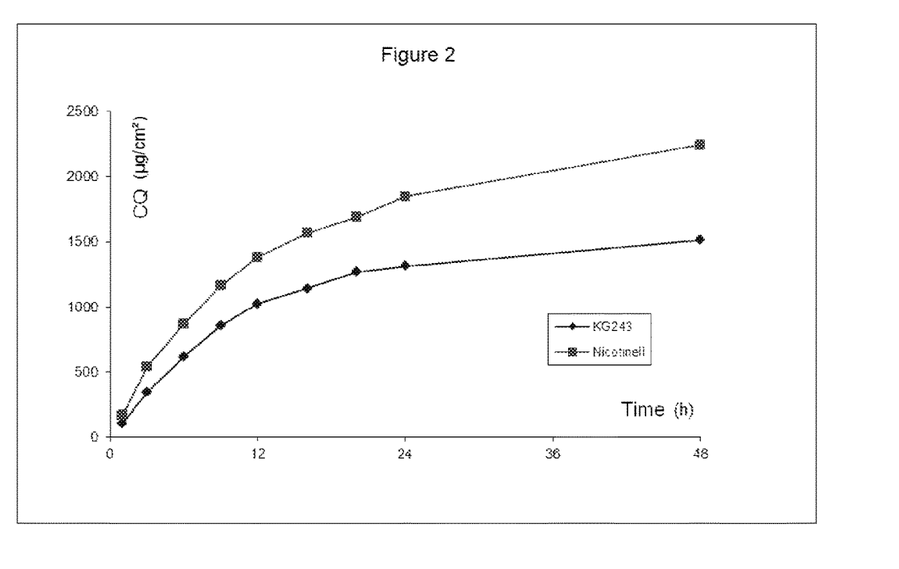

Example 3: Permeation Tests (FIGS. 1 and 2)

The following compositions A and B are obtained according to the process of Example 2:

TABLE 4

|  | KG209 | KG243 |
|---|---|---|
|  | Composition | |
|  | A | B |
| Nicotine base | 11.2% | 11.2% |
| Polymethyl methacrylate/ethylene glycol dimethacrylate copolymer (Microsponge ®) |  | 8.1% |
| Silicone adhesive | 9.0% | 8.1% |
| Acrylate-vinyl acetate copolymer | 79.8% | 72.6% |

In vitro permeation kinetics were carried out on abdominal skin of nude mouse arranged on the surface of a glass (Franz) cell. The results obtained express the comparative cumulative quantities (CQ) from 0 to 48 hours in µg/cm$^2$ between a preparation not containing microporous polymer (formula A) and the reference product (Nicotinell®) (FIG. 1).

| CQ       | 1      | 3      | 6      | 9      | 12      | 16      | 20      | 24      | 48      |
|----------|--------|--------|--------|--------|---------|---------|---------|---------|---------|
| KG209    | 140.47 | 399.50 | 687.86 | 876.30 | 1018.01 | 1176.65 | 1235.77 | 1302.11 | 1504.50 |
| Nicotinell | 67.47 | 249.09 | 514.86 | 737.75 | 933.88  | 1156.95 | 1310.09 | 1449.56 | 1908.67 |

The same preparation is then prepared but containing a quantity of microporous polymer of the cross-linked MMA/GDMA polymer (Microsponge®) type according to the invention (formula B). In vitro permeation kinetics are then carried out on abdominal skin of nude mouse arranged on the surface of a glass (Franz) cell. The results obtained express comparative cumulative quantities (CQ) from 0 to 48 hours in µg/cm² between this preparation according to the invention (formula B) and the reference product (Nicotinell® comprised of a gelled nicotine depot on an adhesive layer) (FIG. 2).

| CQ       | 1      | 3      | 6      | 9       | 12      | 16      | 20      | 24      | 48      |
|----------|--------|--------|--------|---------|---------|---------|---------|---------|---------|
| KG243    | 106.06 | 347.84 | 614.78 | 854.52  | 1024.88 | 1143.59 | 1268.95 | 1313.79 | 1515.68 |
| Nicotinell | 171.45 | 540.27 | 869.15 | 1166.56 | 1382.27 | 1567.33 | 1690.11 | 1849.09 | 2242.83 |

These results show how the presence of a microporous support of the cross-linked MMA/GDMA polymer (Microsponge®) type is able to control the permeation kinetics of nicotine from the matrix patch according to the invention. In particular, the presence of microspheres makes it possible to reduce the quantity of nicotine released in the first 12 hours ("burst" effect observed in FIG. 1 for composition KG209, the curve which crosses that of Nicotinell®) not observed in FIG. 2 for the composition according to the invention. Reduction of the "burst" effect is very important in the case of nicotine in order to avoid a too rapid release of a too large amount of nicotine, an event which may prove to be irritating or toxic.

The experiment was repeated with a formula C differing from formula B wherein the 8.1% of cross-linked MMA/GDMA polymer (Microsponge®) was replaced with 8.1% of lauryl methacrylate/glycol dimethyl methacrylate crosspolymer (Polytrap®). The permeation kinetics results obtained with this formula C were compared with those of formula B and those of Nicotinell obtained during the same experiment so that the results could be directly compared.

|            | Time (hours) |      |      |       |       |
|------------|--------------|------|------|-------|-------|
|            | 0.5          | 1    | 1.5  | 3     | 6     |
| POLYTRAP   | 7.6          | 32.7 | 63.9 | 156.5 | 293.5 |
| MICROSPONGE | 6.2         | 28.3 | 55.8 | 139   | 266.4 |
|            | 12           | 18   | 24   |       |       |
|            | 461.8        | 547.3 | 599.3 |     |       |
|            | 438.9        | 530.5 | 587.6 |     |       |

Figure 4:
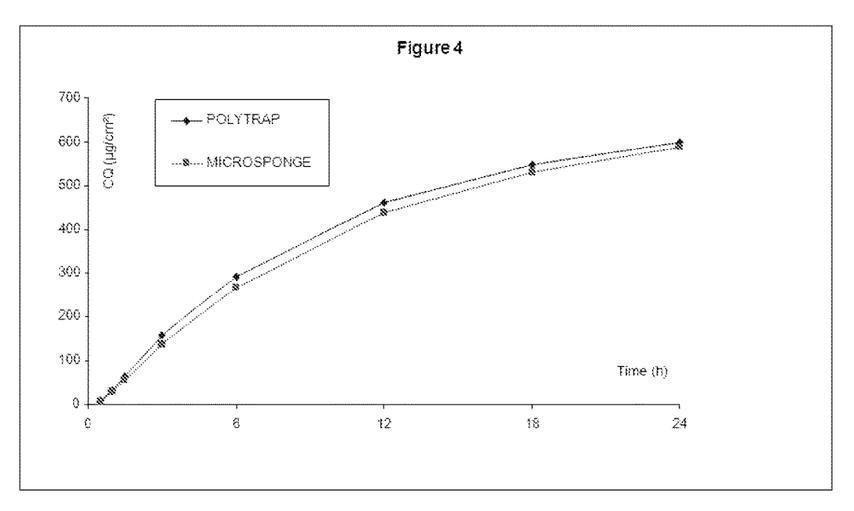
FIG. 4: In vitro permeation kinetics showing the equivalence of the effect of the presence of solid microporous polymer Microsponge® or Polytrap® in the composition according to the invention.

As may be noted in the table above and in appended FIG. 4, the results obtained are comparable when Microsponge® or Polytrap® is used.

The following examples illustrate the influence of the microporous support on the adhesive and cohesive properties of the adhesive matrix containing nicotine.

The following adhesive monolayer compositions C, D and E were obtained following the protocol of Example 2:

TABLE 5

|                                                              | SME416 | SME417 | SME418 |
|--------------------------------------------------------------|--------|--------|--------|
|                                                              | Composition |   |   |
|                                                              | C      | D      | E      |
| Nicotine base                                                | 0%     | 5.0%   | 5.0%   |
| Polymethyl methacrylate/ethylene glycol dimethacrylate copolymer (Microsponge ®) |        | 4.1%   |        |
| Butylhydroxytoluene                                          |        | 0.1%   | 0.1%   |
| Acrylate-vinyl acetate copolymer                             | 100.0% | 90.8%  | 94.9%  |

These compositions are then characterized by adhesion tests, respectively a shear test and a tack test. The shear test consists in measuring the capacity of an adhesive or a self-adhesive formulation such as a patch to resist a static force applied in the same plane. The criterion measured is that of the time required to separate by sliding the material tested from a standard surface such as a steel plate. The longer this time is, the stronger the cohesion. The tack test consists in measuring the force required to unstick, at a given rate, an adhesive or a self-adhesive formulation such as a patch from a standard surface with which it was brought into contact under the effect of low pressure (by setting-up a loop in contact with a probe). The criterion measured is force expressed in Newton. The greater this force is, the greater the tack.

The following results were obtained (Table 4):

TABLE 6

|               | Maximum tack force (Newton) | Shear time         |
|---------------|-----------------------------|--------------------|
| Composition C | 19.2                        | More than 168 hours |
| Composition D | 16.6                        | 112 hours          |
| Composition E | 23.1                        | 86 hours           |

It is thus shown that the addition of nicotine, by a plasticizing effect, within an adhesive decreases the cohesion of the system (reduction in shear time) and increases its tack (compared between compositions C and E). The addition of porous microparticles of the cross-linked MMA/GDMA polymer (Microsponge®) type improves the cohesion of the system and reduces tack strength (compared between compositions D and E). The addition of porous microparticles of the cross-linked MMA/GDMA polymer (Microsponge®) type thus unexpectedly reduces the plasticizing effect of nicotine.

Example 5: Influence of Adhesive on Nicotine Release

The following examples illustrate, for the preparations of compositions according to the invention, the influence of the adhesive on nicotine release.

The following adhesive monolayer compositions were obtained following the protocol of Example 2:

TABLE 7

|  | KG427 | KG428 | KG429 |
|---|---|---|---|
| Nicotine base | 10.0% | 10.0% | 10% |
| Polymethyl methacrylate/ethylene glycol dimethacrylate copolymer | 8.3% | 8.3% | 8.3% |
| Butylhydroxytoluene | 0.1% | 0.1% | 0.1% |
| Self-cross-linking acrylate-vinyl acetate adhesive (Duro-Tak ® 2052) | 81.6% | | |
| Non-cross-linked acrylic adhesive (Duro-Tak ® 9088) | | 81.6% | |
| Self-cross-linking acrylate-vinyl acetate adhesive (Duro-Tak ® 2196) | | | 81.6% |

Figure 3:
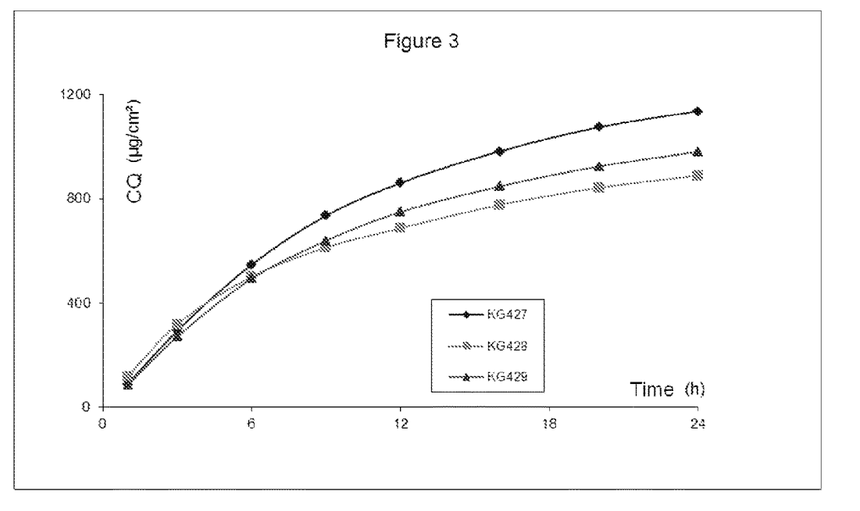
FIG. 3: Adhesive monolayer compositions and permeation results according to the adhesive used.

The in vitro permeation test was performed according to the description provided in preceding Example 3 and the results obtained are those of FIG. 3.

| CQ | 1 | 3 | 6 | 9 | 12 | 16 | 20 | 24 |
|---|---|---|---|---|---|---|---|---|
| KG427 | 90 | 294 | 547 | 735 | 860 | 983 | 1076 | 1137 |
| KG428 | 118 | 319 | 501 | 613 | 687 | 776 | 842 | 888 |
| KG429 | 87 | 271 | 493 | 639 | 749 | 847 | 924 | 982 |

The use of porous microparticles of the cross-linked MMA/GDMA polymer (Microsponge®) type makes it possible to obtain for a patch a similar in vitro kinetics profile whatever adhesive is used.

The invention claimed is:

1. A self-adhesive transdermal device including the association of a support layer and a self-adhesive matrix layer and a detachable protective film, said self-adhesive matrix layer allowing the device to adhere to the skin for at least 12 hours and said self-adhesive matrix layer including:
   a. 65 to 93% by weight in relation to the total weight of the self-adhesive matrix layer of at least one self-adhesive polymer selected from the group comprising polymers of acrylic or acrylate, and is comprised of monomers selected from the group comprising vinyl acetate, 2-ethylhexyl acrylate, butyl acrylate, acrylic acid, methyl methacrylate, methyl acrylate, tert-octyl acrylamide, 2-hydroxy ethyl acrylate, glycidyl methacrylate, or mixtures thereof; and
   b. 2 to 15% by weight in relation to the total weight of the self-adhesive matrix layer of at least one microporous solid polymer in the form of microparticles, said microporous solid polymer being comprised of monomer units selected from the group of monomers comprising methyl methacrylate, ethylene glycol dimethacrylate, lauryl methacrylate, glycol dimethacrylate, and mixtures thereof, said microparticles having an average size comprised between 1 μm and 100 μm said microparticles being distributed within the self-adhesive polymer mass and said microparticles containing nicotine at 5 to 20% by weight in relation to the total weight of the self-adhesive matrix layer, wherein the device has an average nicotine delivery rate from the matrix layer comprised between 10 μg/cm²/h and 50 μg/cm²/h, during a time interval comprised between 1 and 24 hours.

2. The device according to claim 1, wherein the monomers are selected from the group comprising acrylic acid, butyl acrylate, 2-ethylhexyl acrylate, vinyl acetate, or mixtures thereof.

3. The device according to claim 1, wherein the microporous solid polymer is comprised of monomer units of ethylene glycol dimethacrylate and of methyl methacrylate.

4. The device according to claim 1, wherein the microporous solid polymer microparticles are distributed homogeneously within the self-adhesive polymer mass.

5. The device according to claim 1, wherein the nicotine is adsorbed homogeneously in the microporous solid polymer mass.

6. The device according to claim 1, wherein the self-adhesive matrix layer includes at least one antioxidant agent selected from the group comprising butylhydroxytoluene (BHT), butyl hydroxy anisole (BHA), ascorbyl palmitate, alpha tocopherol and esters thereof, citric acid, propyl gallate and mixtures thereof.

7. The device according to claim 6, wherein the antioxidant agent is present in said self-adhesive matrix layer, in relation to the total weight of said self-adhesive matrix layer, in a proportion comprised between 0.01 and 1% by weight.

8. The device according to claim 1, wherein said microporous solid polymer microparticles have an average size comprised between 5 μm and 50 μm.

9. The device according to claim 1, wherein said microporous solid polymer microparticles have an average size comprised between 15 μm and 30 μm.

10. A method for preparing a transdermal device according to claim 1, comprising the following steps:
    a. mixing the self-adhesive polymer selected from the group comprising polymers of acrylic or acrylate, and is comprised of monomers selected from the group comprising vinyl acetate, 2-ethylhexyl acrylate, butyl acrylate, acrylic acid, methyl methacrylate, methyl acrylate, tert-octyl acrylamide, 2-hydroxy ethyl acrylate, glycidyl methacrylate, or mixtures thereof, the microporous solid polymer in the form of microparticles, said microporous solid polymer being comprised of monomer units selected from the group of monomers comprising methyl methacrylate, ethylene glycol dimethacrylate, lauryl methacrylate, glycol dimethacrylate, and mixtures thereof, said microparticles having an average size comprised between 1 μm and 100 μm, nicotine and optionally the oxidizing agent until a homogeneous mixture is obtained;
    b. coating the homogeneous mixture obtained in step a. on a detachable protective film;
    c. gradually drying the coated mixture;
    d. laminating the product obtained in step c. onto a support layer; and
    e. optionally, cutting the product obtained in step d. in such a way as to obtain transdermal devices or patches of the desired size.

11. A self-adhesive transdermal device including the association of a support layer and a self-adhesive matrix layer and a detachable protective film, said self-adhesive matrix layer allowing the device to adhere to the skin for at least 12 hours and said self-adhesive matrix layer including:
    a. 65 to 93% by weight in relation to the total weight of the self-adhesive matrix layer of at least one self-adhesive polymer selected from the group comprising polymers of acrylic or acrylate and is comprised of monomers selected from the group comprising vinyl acetate, 2-ethylhexyl acrylate, butyl acrylate, acrylic acid, methyl methacrylate, methyl acrylate, tert-octyl acrylamide, 2-hydroxy ethyl acrylate, glycidyl methacrylate, or mixtures thereof; and b. 2 to 15% by weight in relation to the total weight of the self-adhesive matrix layer of at least one microporous solid polymer in the form of microparticles, said microporous solid polymer being comprised of monomer units selected from the group of monomers comprising methyl methacrylate and ethylene glycol dimethacrylate, and mixtures thereof, said microparticles having an average size comprised between 1 µm and 100 µm said microparticles being distributed within the self-adhesive polymer mass and said microparticles containing nicotine at 5 to 20% by weight in relation to the total weight of the self-adhesive matrix layer.

12. The device according to claim 11, wherein the monomers are selected from the group comprising acrylic acid, butyl acrylate, 2-ethylhexyl acrylate, vinyl acetate, or mixtures thereof.

13. The device according to claim 11, wherein said microporous solid polymer has a total pore volume comprised between 0.5 ml/g and 3.0 ml/g.

14. The device according to claim 11, wherein said microporous solid polymer has a granular pore volume comprised between 0.2 ml/g and 3.0 ml/g.

15. The device according to claim 11, wherein the microporous solid polymer microparticles are distributed homogeneously within the self-adhesive polymer mass.

16. The device according to claim 11, wherein the nicotine is adsorbed homogeneously in the microporous solid polymer mass.

17. The device according to claim 11, wherein the basis weight of the self-adhesive matrix layer is comprised between 50 and 300 $g/m^2$.

18. The device according to claim 11, wherein the self-adhesive matrix layer includes at least one antioxidant agent selected from the group comprising butylhydroxytoluene (BHT), butyl hydroxy anisole (BHA), ascorbyl palmitate, alpha tocopherol and esters thereof, citric acid, propyl gallate and mixtures thereof.

19. The device according to claim 18, wherein the antioxidant agent is present in said self-adhesive matrix layer, in relation to the total weight of said self-adhesive matrix layer, in a proportion comprised between 0.01 and 1% by weight.

20. The device according to claim 17, wherein the basis weight is comprised between 100 $g/m^2$ and 200 $g/m^2$.

21. The device according to claim 11, wherein said microporous solid polymer microparticles have an average size comprised between 5 µm and 50 µm.

22. The device according to claim 11, wherein said microporous solid polymer microparticles have an average size comprised between 15 µm and 30 µm.

23. The device according to claim 13, wherein said microporous solid polymer has a total pore volume comprised between 1 ml/g and 2 ml/g.

24. The device according to claim 14, wherein said microporous solid polymer has a granular pore volume comprised between 0.5 ml/g and 1.5 ml/g.

25. A method for treating nicotine addiction comprising the application to a person in need thereof of a self-adhesive transdermal device according to claim 11.

26. A method for treating neurodegenerative diseases comprising the application to a person in need thereof of a self-adhesive transdermal device according to claim 11.

* * * * *